(12) United States Patent
Revie et al.

(10) Patent No.: US 6,254,641 B1
(45) Date of Patent: Jul. 3, 2001

(54) CEMENT PRESSURIZER WITH FLANGE

(75) Inventors: Ian Revie, Boroughbridge; Brian Griffiths, Lymington, both of (GB); Gareth Steer, Princeton, NJ (US); Martin Lukoschek; Steffen Breusch, both of Neckargemund (DE); Bodo Fischer, Karlsruhe (DE)

(73) Assignee: Johnson & Johnson Medical Limited, Berks ( * ) Notice: Subject to any disclaimer, the term of this patent is extended or adjusted under 35 U.S.C. 154(b) by 0 days.

(21) Appl. No.: 09/362,978

(22) Filed: Jul. 28, 1999

(30) Foreign Application Priority Data

Jul. 31, 1998 (GB) .................................................. 9816742

(51) Int. Cl.[7] ........................................................ A61F 2/36
(52) U.S. Cl. .......................................... 623/23.48; 606/94
(58) Field of Search ............................ 623/23.48, 22.12, 623/23.46, 23.21, 23.22; 606/94, 95

(56) References Cited

U.S. PATENT DOCUMENTS

| 4,274,163 | * | 6/1981 | Malcom et al. | 623/23.48 |
| 4,595,006 | * | 6/1986 | Burke et al. | 128/303 |
| 4,783,192 | * | 11/1988 | Wroblewski et al. | 623/16 |
| 4,815,454 | * | 3/1989 | Dozier, Jr. | 606/94 |
| 5,741,265 | * | 4/1998 | Chan | 606/94 |

* cited by examiner

Primary Examiner—Paul B. Prebilic

(57) ABSTRACT

A pressurizer device (1) is provided with a body (6) in the form of a collar and a surrounding radially extending flexible flange (8). A prosthetic component to be disposed in a cemented bone cavity is inserted through the central opening (50) in the body (6). Pressure in the bone cement is maintained during insertion of the prosthetic component by the flange (8) being held down around the prosthetic component during insertion.

9 Claims, 4 Drawing Sheets

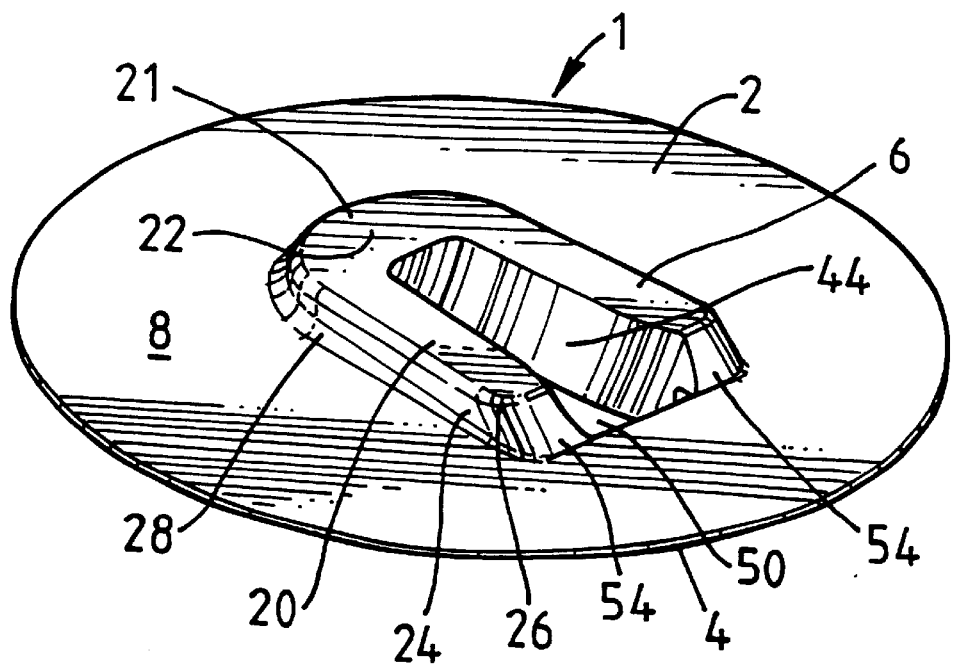
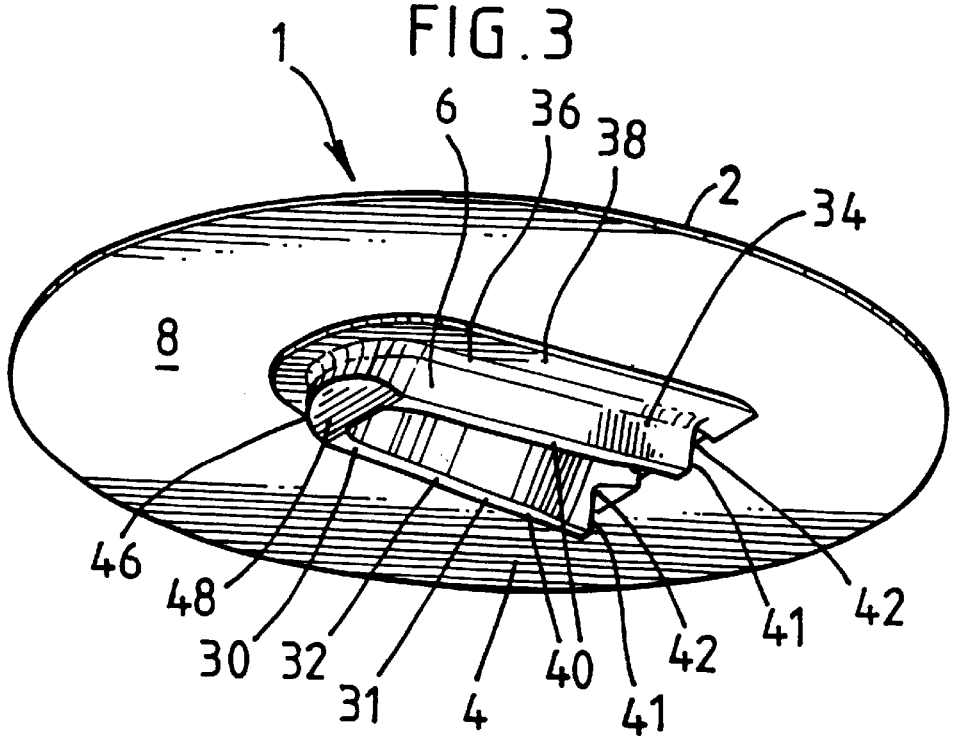

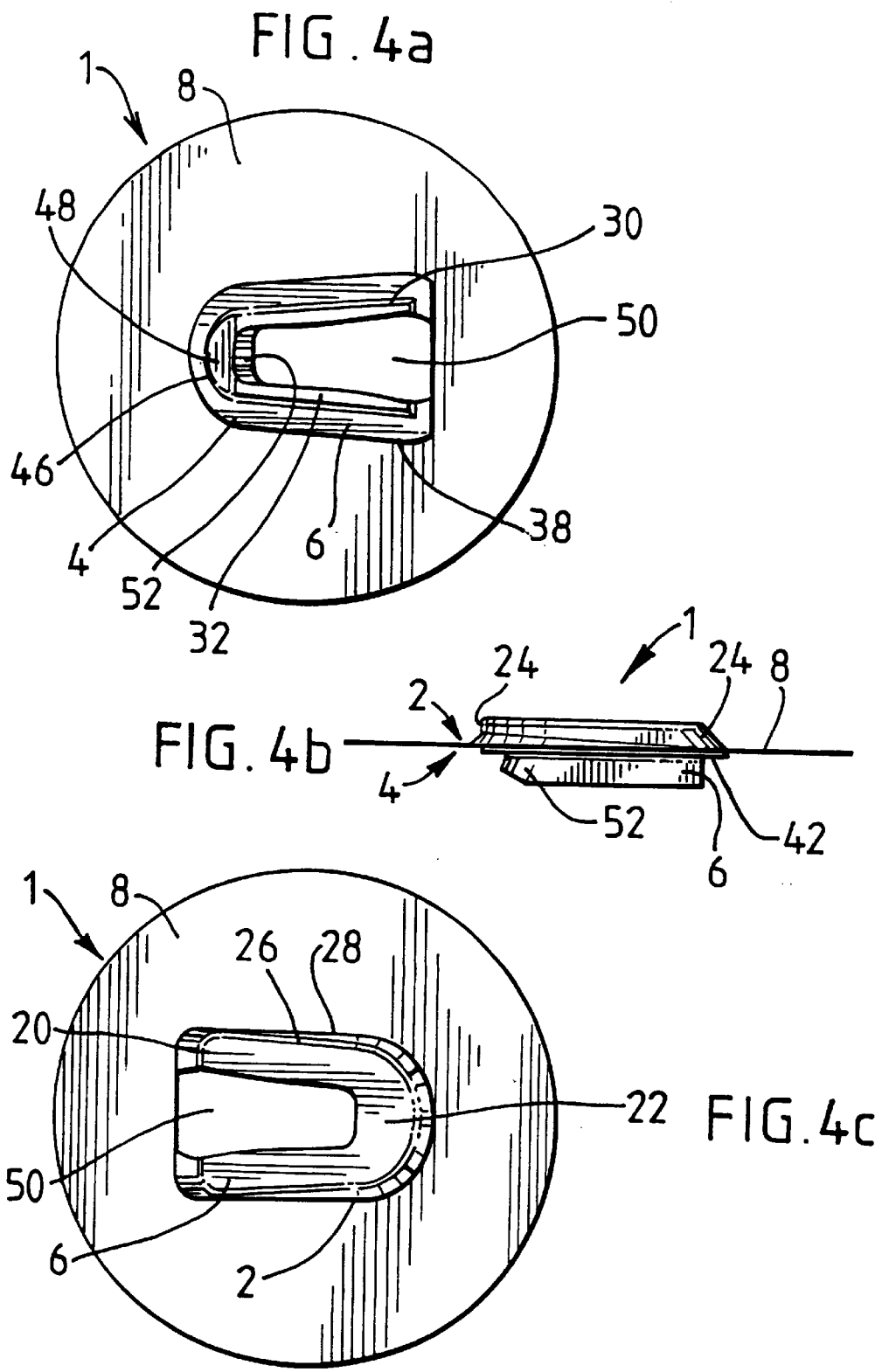

CEMENT PRESSURIZER WITH FLANGE

The present invention relates to a pressuriser device particularly for use in cemented femoral hip stem replacement. The pressuriser device is also suitable for use in other cemented prosthetic applications.

A femoral bone is prepared for a replacement hip stem prosthesis by expanding the internal cavity of the femoral bone by using a broach or rasp. The broached cavity is filled with bone cement either before or after the insertion of the hip stem prosthesis.

In the method in which a hip stem prosthesis is inserted after the cement is introduced into the broached cavity, it is important to centralise the stem within the prepared femoral cavity and to maintain the pressure of the cement surrounding the hip stem prosthesis. Centralisation of a hip stem prosthesis and pressurisation of the cement have been linked to long term stem survivability in hip replacement surgery.

According to the present invention, there is provided a pressurisation device in the form of a collar defining an opening for accommodating a prosthetic component, wherein the collar is surrounded by a radially extending flexible flange.

Preferably, the flexible flange extends radially from the hollow collar such that the collar has an upper body portion above the flexible flange and a lower body portion below the flexible flange.

The upper and lower body portions may comprise generally U-shaped members. Preferably, the internal profile of the upper body portion is adapted to correspond to the prosthetic component.

Preferably, the upper and lower body portions have sealing lips in which the flexible flange is sealed.

The external profile of the lower body portion may be shaped to correspond to a bone cavity in which the prosthetic component is to be disposed.

The upper body portion may optimally have a shoulder adjacent the U-shaped member which, in use, rests on the entrance to the bone cavity in which the prosthetic component is to be disposed.

Preferably, the flexible flange is transparent to allow clarity of positioning. Preferably, the prosthetic component is a prosthetic hip stem and the bone cavity is a femoral canal.

Preferably, the upper and lower body portions are formed of silicon rubber. The sealing lips of the upper and lower bodies may be approximately 3 millimeters thick.

Preferably, the flexible flange is between 0.5 and 1 millimeter thick. Preferably, the flexible flange has a diameter of approximately 10 centimeters.

The pressuriser device may be supplied in varying sizes to suit the bone cavity.

An embodiment of a pressuriser device in accordance with the present invention will now be described, by means of example only, with reference to the accompanying drawings in which:

FIG. 2 is a perspective view of the upper side of a pressuriser device in accordance with the present invention;

FIG. 3 is a perspective view of the underside of the pressuriser device of FIG. 2;

FIGS. 4a, 4b and 4c are a top plan, side view and underneath plan of the cement pressuriser of FIG. 2;

Figure 1:
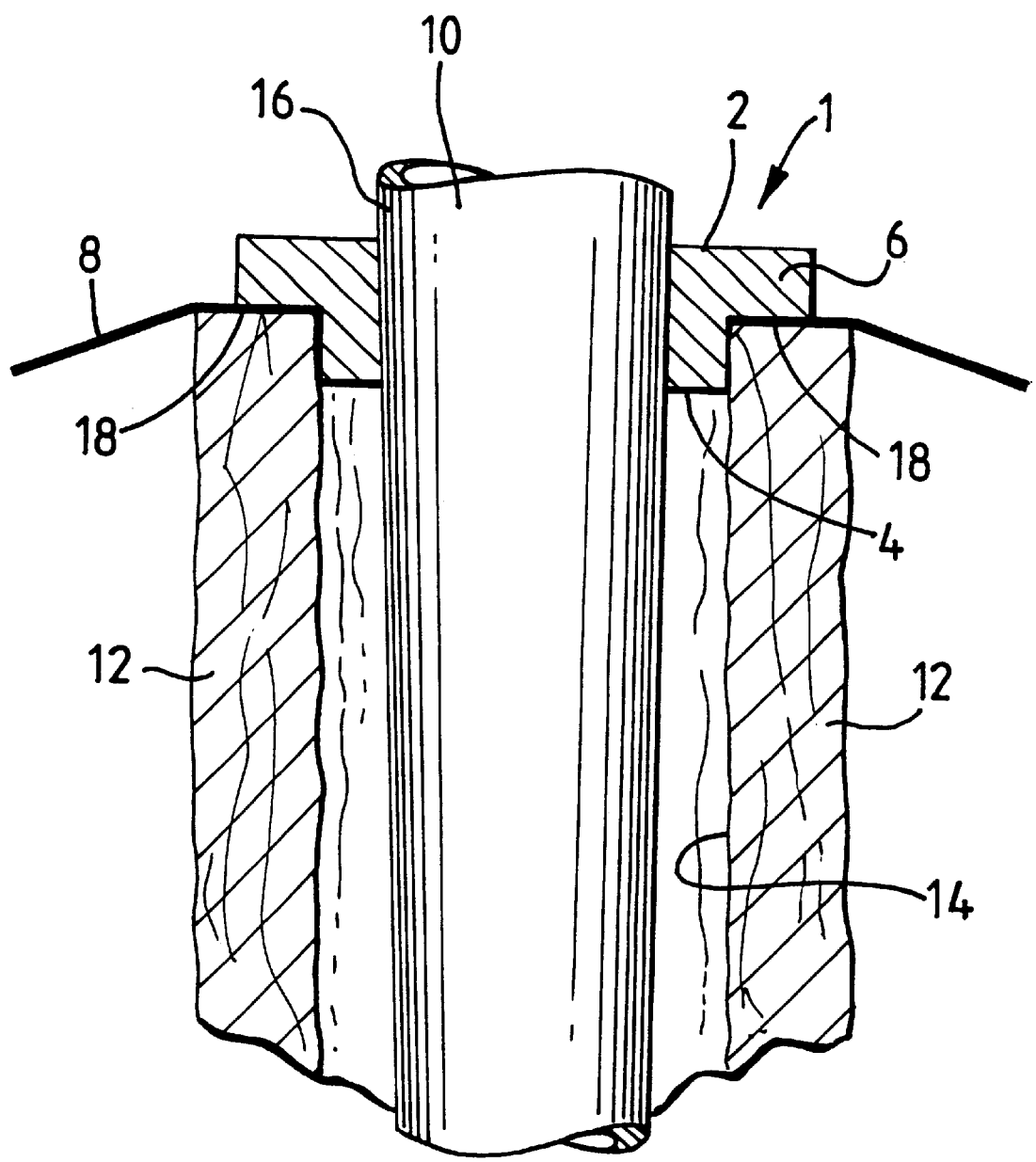
FIG. 1 is a cross-section of the pressuriser device in accordance with the present invention in situ between a prosthetic hip stem and femoral canal.
Figure 5A:
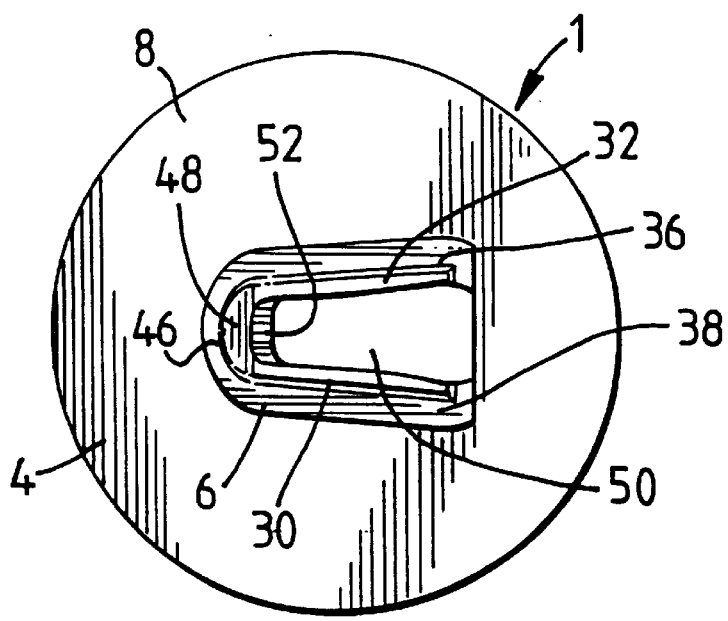
FIGS. 5a, 5b and 5c are a top plan, cross-section and underneath plan of the cement pressuriser of FIG. 2.
Figure 5B:
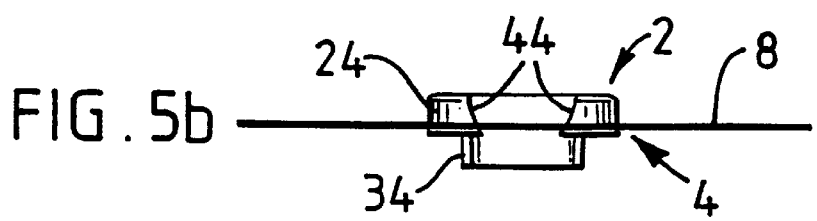
Figure 5C:
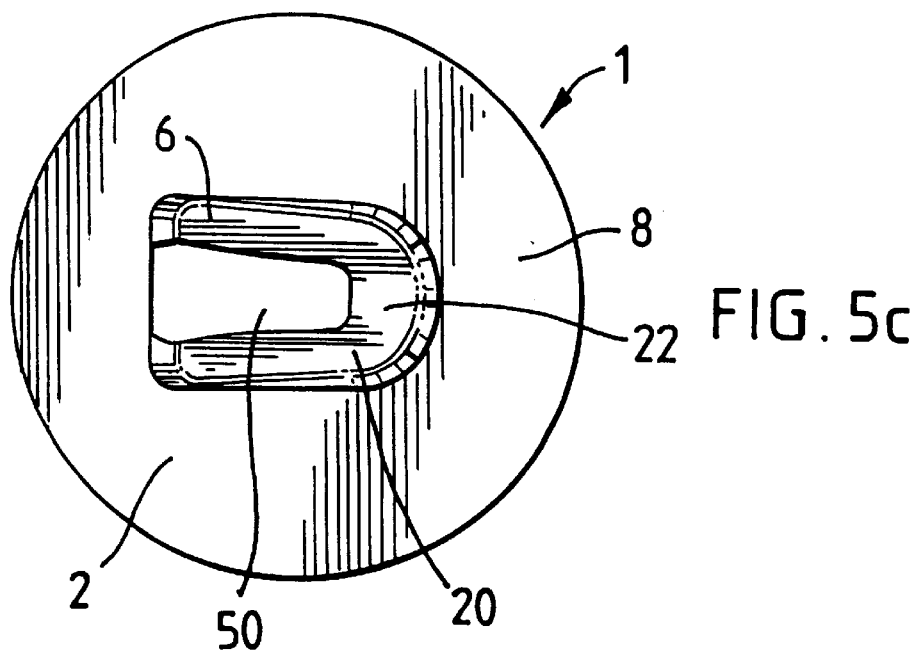

Referring to the drawings, there is provided a pressuriser device 1 with an upper side 2 and an underneath side 4. The pressuriser device 1 has a collar in the form of a body portion 6 and a radially surrounding flexible flange 8.

The present invention will be described in relation to a prosthetic hip stem for insertion in a femoral canal by means of a cement mantle. However, the pressuriser device 1 is suitable for use with any form of cemented prosthetic component.

FIG. 1 shows the position of a pressuriser device 1 at the opening of a femoral cavity 14. The surrounding femur 12 has been broached to increase the size of the cavity 14 within it. The cavity 14 is filled with cement before insertion of a femoral stem 10. The pressuriser device 1 sits on the femur lip 18 at the entrance to the cavity 14. The hip stem 10 is inserted through a central opening 50 in the body 6 of the pressuriser device 1.

The pressuriser device 1 has an upper portion 20 of a body 6, the upper portion 20 including a generally U-shaped member 21. The U-shaped member 21 has a flat top surface 22 with supporting walls 24. The walls 24 are generally vertical except at the open ends 54 of the U-shaped member 21 which are angled away from the top surface 22 towards their base. The upper portion 20 also has a sealing lip 28 generally surrounding the U-shaped member 21 and the lip 28 has a greater width at the curved portion of the U-shaped member 21 than at the open ends 54.

The walls 24 and the flat top surface 22 of the U-shaped member 21 are joined by an bevelled surface 26.

The inner walls 44 of the upper portion 20 of the body 6 have a profile which is curved to correspond to the external shape of the hip stem 10. The inner walls 44 define the central opening 50 in the body 6.

The flange 8 extends from the sealing lip 28 radially to form a flexible extension around the body 6.

The body 6 has an underneath portion 30 with a U-shaped member 31 of thinner dimensions than the U-shaped member 21 of the upper protion 20.

The U-shaped member 31 of the underneath portion 30 is surrounded by an outer lip 38 with a curved lip 36 joining the outer lip 38 to the base of the U-shaped member 31.

The U-shaped member 31 of the underneath portion 30 has a flat top surface 32 with supporting walls 34. The walls 34 are generally vertical. The curved end 46 of the U-shaped member 31 has an angled top surface 48 angled from the flat top surface 32 towards the surrounding outer lip 38.

The legs 40 of the U-shaped member 31 have free ends 41 with cut-away portions 42 such that the free ends 41 are abrupt and vertical and within the U-shape defined by the upper portion 20.

The external profile of the underneath portion 30 corresponds to the shape of the broached cavity 14 in the bone. The surrounding outer lip 38 forms a shoulder which rests on the opening 18 to the bone cavity 14.

The flange 8 is attached or moulded into the body 6 between the outer lip 38 of the underneath portion 30 and the upper sealing lip 28 of the upper portion 20 of the body 6. The flange 8 is transparent to allow clarity of positioning of the pressuriser device 1.

The flange 8 has a diameter of approximately 10 centimeters and is 0.5 to 1 millimeter thick. The sealing lip 28 and the outer lip 38 are approximately 3 millimeters thick.

The body 6 is formed of silicon rubber and, in this example, is provided in six sizes corresponding to different sizes of the femoral bone.

In use, the pressuriser device 1 is positioned at the entrance 18 to a cement filled femoral cavity 14 and a hip stem 10 is inserted through the central opening 50 in the body 6 of the pressuriser device 1. The hip stem 10 is inserted until it is correctly positioned within the central opening 50. The transparent flexible flange 8 maintains the pressure in the cement within the cavity 14. The flange 8 is held down by the surgeon's hand around the femur 12 as the hip stem 10 is inserted.

Modifications and improvements can be made to the foregoing without departing from the scope of the present invention.

What is claimed is:

1. A pressurization device in the form of a collar defining an opening for accommodating a prosthetics component, said collar having a U-shaped upper body portion extending above a radially extending flexible flange and a U-shaped lower body portion extending below the flange; said upper and lower body portions having sealing lips, said flange surrounding said collar and sealed to said sealing lips.

2. A pressurization device as claimed in claim 1 wherein the upper body portion has a flat top surface and supporting walls and the inner supporting walls have a profile adapted to correspond to a prosthetic component.

3. A pressurization device as claimed in claim 2 wherein the lower body portion has supporting walls and a flat surface and the supporting walls are adapted to correspond to the shape of the bone cavity in which the prosthetic component is to be installed.

4. A pressurization device as claimed in claim 3 wherein the U-shaped upper body portion has a shoulder adapted to rest on the entrance to the bone cavity in which the prosthetic component is to be disposed.

5. A pressurisation device as claimed in claim 4, wherein the flexible flange is transparent to allow clarity of positioning.

6. A pressurisation device as claimed in claim 4, wherein the upper and lower body portions are formed of silicon rubber.

7. A pressurisation device as claimed in claim 1, wherein the sealing lips of the upper and lower bodies are approximately 3 millimeters thick.

8. A pressurisation device as claimed in claim 1, wherein the flexible flange is between 0.5 and 1 millimeter thick.

9. A pressurisation device as claimed in claim 1, wherein the flexible flange has a diameter of approximately 10 centimeters.

* * * * *